United States Patent
Brader et al.

(10) Patent No.: US 6,531,620 B2
(45) Date of Patent: Mar. 11, 2003

(54) CYCLIC SILAZANES

(75) Inventors: Leonhard Brader, Fischbachau (DE);
Oliver Schäfer, München (DE);
Andreas Bauer, München (DE);
Volker Frey, Burghausen (DE); Bernd Pachaly, Mehring-Öd (DE)

(73) Assignee: Consortium fur Elecktrochemische Industrie GmbH, Munich (DE)

( * ) Notice: Subject to any disclaimer, the term of this patent is extended or adjusted under 35 U.S.C. 154(b) by 0 days.

(21) Appl. No.: 09/965,902

(22) Filed: Sep. 27, 2001

(65) Prior Publication Data

US 2002/0042491 A1 Apr. 11, 2002

(30) Foreign Application Priority Data

Oct. 5, 2000 (DE) .......................... 100 49 183

(51) Int. Cl.⁷ ................. C07F 7/10; C07F 7/08
(52) U.S. Cl. ............... 556/413; 556/407; 556/410; 556/412; 556/425; 556/466; 556/467
(58) Field of Search ................ 556/407, 410, 556/412, 413, 425, 466, 467

(56) References Cited

U.S. PATENT DOCUMENTS

| | | | |
|---|---|---|---|
| 3,146,250 A | | 8/1964 | Speier |
| 4,499,234 A | * | 2/1985 | Pratt et al. .................. 524/783 |
| 4,584,393 A | | 4/1986 | Webb et al. |
| 4,806,666 A | * | 2/1989 | Pillot et al. .................. 556/425 |
| 5,026,890 A | * | 6/1991 | Webb et al. ................. 556/445 |
| 5,739,201 A | * | 4/1998 | Ugai et al. ..................... 528/34 |

FOREIGN PATENT DOCUMENTS

| | | | |
|---|---|---|---|
| DE | 35 46 376 A1 | 7/1986 | |
| DE | 4234846 A1 | * 4/1994 | ......... C08G/77/388 |

OTHER PUBLICATIONS

Derwent Abstract Corresponding To DE 35 46 376 [AN 1986–125089].

* cited by examiner

Primary Examiner—Margaret G. Moore
Assistant Examiner—Jeffrey B. Robertson
(74) Attorney, Agent, or Firm—Brooks & Kushman P.C.

(57) ABSTRACT

The invention relates to cyclic silazanes of the formula II

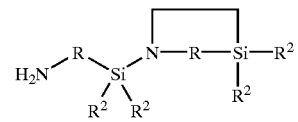

in which

R is a divalent, Si—C and C—N-bound, optionally cyano- or halogen-substituted $C_3$–$C_{15}$–hydrocarbon radical, in which one or more, non-adjacent methylene units may be replaced by —O—, —CO—, —COO—, —OCO—, —OCOO—, —S— or —$NR^x$— groups and in which one or more non-adjacent methine units may be replaced by —N=, —N=N— or —P= groups, where at least 3 and at most 6 atoms are arranged between the silicon atom and the nitrogen atom of the ring, $R^x$ is hydrogen or an optionally halogen-substituted $C_1$–$C_{10}$-hydrocarbon radical, and $R^2$ is a hydrogen atom or a monovalent, optionally cyano- or halogen-substituted, Si-C-bound $C_1$–$C_{20}$-hydrocarbon radical or $C_1$–$C_{20}$-hydrocarbon-oxy radical, in each of which one or more non-adjacent methylene units may be replaced by —O—, —CO—, —COO—, —OCO—, —OCOO—, —S— or —$NR^x$— groups and in which one or more non-adjacent methine units may be replaced by —N=, —N=N— or —P= groups.

8 Claims, No Drawings

CYCLIC SILAZANES

BACKGROUND OF THE INVENTION

1. Field of the Invention

The invention relates to cyclic silazanes, to a process for the preparation thereof, and to reactions thereof with water and alcohols.

2. Background Art

Cyclic silazanes can be used, for example, as precursors for the preparation of aminoalkyl-terminated polysiloxanes. If cyclic silazanes are hydrolyzed as described in DE-A-3546376, bisaminoalkyl-terminated disiloxanes are obtained:

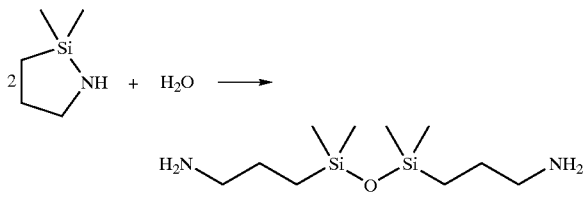

DE-A-3546376 also discloses cyclic silazanes which are prepared by intramolecular hydrosilylation, in particular N-substituted silazanes which carry an $SiY_2H$ group as a substituent, where Y is a hydrocarbon radical. The hydrolysis of these silazanes also gives, besides the desired bisaminoalkyl-terminated disiloxanes, monoamino-alkyl-substituted disiloxanes and unsubstituted tetraalkyldisiloxanes:

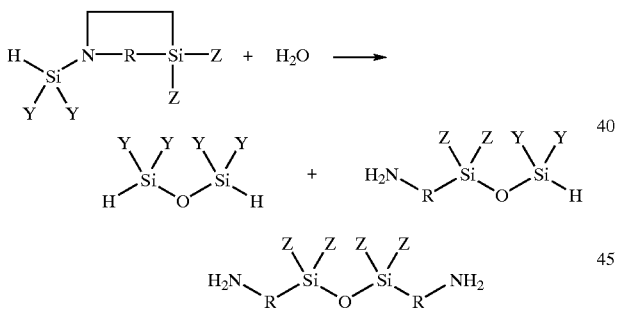

Z is as defined for Y.

Cyclic silazanes which are silyl-substituted on the nitrogen were described for the first time in U.S. Pat. No. 3,146,250. The silyl substituents have the general formula I $$SiY_2—R'—X \qquad (I)$$

where Y is a hydrocarbon radical, R' is a divalent hydrocarbon, and X is a halogen atom having an atomic weight of greater than 35 daltons. The hydrolysis of these silyl-substituted cyclic silazanes also gives, besides the desired bisaminoalkyl-terminated disiloxanes, monochloroalkyl-substituted disiloxanes and bischloroalkyl-substituted disiloxanes.

SUMMARY OF INVENTION

The invention relates to cyclic silazanes of the general formula II

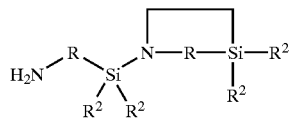

in which
R is a divalent, Si—C— and C—N-bound, optionally cyano- or halogen-substituted $C_3$–$C_{15}$-hydrocarbon radical, in which one or more non-adjacent methylene units may be replaced by —O—, —CO—, —COO—, —OCO—, —OCOO—, —S— or —$NR^x$— groups and in which one or more non-adjacent methine units may be replaced by —N=, —N=N— or —P= groups, where at least 3 and at most 6 atoms are arranged between the silicon atom and the nitrogen atom of the ring,
$R^2$ is a hydrogen atom or a monovalent, optionally cyano- or halogen-substituted, Si—C-bound $C_1$–$C_{20}$-hydrocarbon radical or $C_1$–$C_{20}$-hydrocarbonoxy radical, in each of which one or more non-adjacent methylene units may be replaced by —O—, —CO—, —COO—, —OCO—, —OCOO—, —S— or —$NR^x$— groups, in which one or more non-adjacent methine units may be replaced by —N=, —N=N— or —P=groups, and wherein
$R^x$ is hydrogen or an optionally halogen-substituted $C_1$–$C_{10}$-hydrocarbon radical, and
The compounds of the general formula II contain two Si-alkyl-nitrogen radicals and no Si-alkyl-halogen radical. The compounds of the general formula II are then hydrolyzed, forming bisaminoalkyl-terminated disiloxanes of the general formula III in high yields and essentially without further by-products:

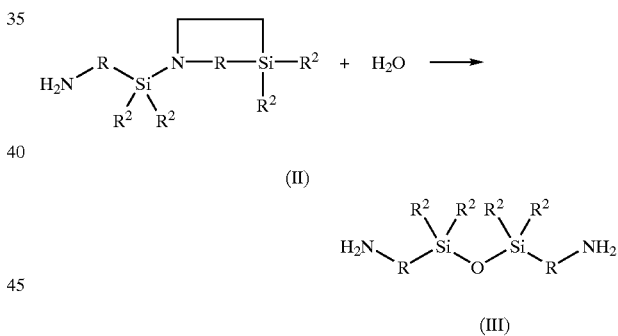

This process for the preparation of bisaminoalkyl-terminated disiloxanes of the general formula III is likewise a subject-matter of the invention.

R may be aliphatically saturated or unsaturated, aromatic, straight- chain or branched. R is preferably an unbranched $C_3$–$C_4$-alkylene radical, which may be substituted by halogen atoms, in particular, fluorine and/or chlorine.

The $C_1$–$C_{20}$-hydrocarbon radicals and $C_1$–$C_{20}$-hydrocarbonoxy radicals $R^2$ may be aliphatically saturated or unsaturated, aromatic, straight-chain or branched. $R^2$ preferably has 1 to 12 atoms, in particular 1 to 6 atoms, preferably only carbon atoms, or one alkoxy oxygen atom and otherwise only carbon atoms. $R^2$ is preferably a straight-chain or branched $C_1$–$C_6$-alkyl radical. Particular preference is given to the radicals methyl, ethyl, phenyl, vinyl and trifluoropropyl.

Particular preference is given to the compounds in which R is a propylene radical and $R^2$ is a methyl, ethyl, phenyl, vinyl or trifluoropropyl radical.

The compounds of the general formula II may be reacted with alcohols of the general formula R³—OH, forming aminoalkyl-terminated dialkylalkoxysilanes of the general formula VI, likewise in high yields and also essentially without further by-products.

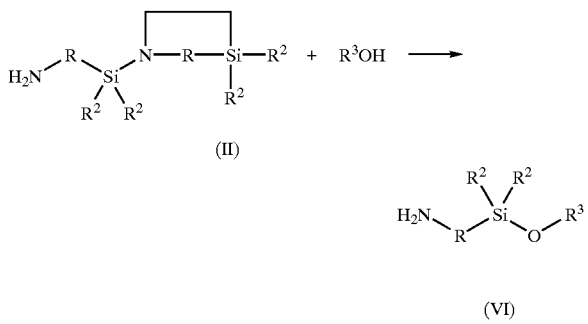

(II)

(VI)

R² and R here are as defined above, and R³ is a monovalent, optionally cyano- or halogen-substituted $C_1$–$C_{20}$-hydrocarbon radical, in which one or more non-adjacent methylene units may be replaced by —O—, —CO—, —COO—, —OCO— or —OCOO— groups, —S— or —NR$^x$— where R$^x$ is as defined above, and in which one or more non-adjacent methine units may be replaced by —N=, —N=N— or —P= groups and may optionally carry further OH groups. This process for the preparation of aminoalkyl-terminated dialkylmethoxysilanes of the general formula III is likewise a subject-matter of the invention. R³ is preferably methyl, ethyl, isopropyl or methoxymethyl.

The invention furthermore relates to a process for the preparation of the cyclic silazanes of the general formula II in which a haloalkyldialkylchlorosilane of the general formula IV

(IV)

or bis(haloalkyl)tetraalkyldisilazane of the general formula V

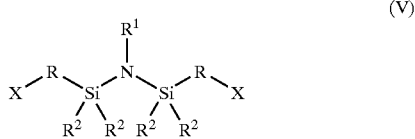

(V)

or a mixture of compounds of the general formulae IV and V, in which
x is F, Cl, Br or I,
R¹ is a hydrogen atom or a monovalent, optionally halogen-substituted, Si—C-bound $C_1$–$C_{15}$-hydrocarbon radical in which in each case one or more non-adjacent methylene units may be replaced by —O—, —CO—, —COO—, —OCO— or —OCOO— groups or —S— and in which one or more non-adjacent methine units may be replaced by —N=, —N=N— or —P= groups, and
R² and R are as defined above, is reacted with ammonia.

The process disclosed in DE-A-3546376 for the preparation of silazanes which are silyl-substituted on the nitrogen uses expensive starting materials which are difficult to prepare. The process described in U.S. Pat. No. 3,146,250 gives only low yields of the desired product. By contrast, the above process gives the compounds of the general formula II inexpensively, i.e. from inexpensive starting materials and in high yields.

A characterizing feature of this process is that the ammonia in this process is simultaneously reactant, but also acceptor for the hydrogen halide liberated and, at sufficient pressure, is additionally also a solvent. The ammonia is therefore employed in stoichiometric amounts or in excess, based on the compounds of the general formulae IV and V. Preference is given to a 10- to 140-fold molar excess, particularly preferably to a 30- to 70-fold molar excess.

In order to accelerate the reaction, catalysts may optionally be added, for example metal halides such as sodium iodide or potassium iodide. In a preferred embodiment, the reaction components should be actively mixed. In order to ensure good mixing of the reaction components, the reaction can be carried out, for example, with stirring. The reaction temperature is limited at the lower end by the solubility of the reaction components and at the upper end by the decomposition temperatures of the starting materials and products. The process is preferably carried out at from 0° C. to 150° C., preferably at above room temperature. A reaction temperature of at least 40° C., in particular at least 60° C., is particularly preferred.

It is advantageous to carry out the reaction at a superatmospheric pressure of from 1.1 to 1000 bar. In a preferred embodiment, the pressure is at least 20 bar. The pressure can varied by admixing an inert gas if desired. The compounds of the general formula II are isolated and purified by known industrial methods, such as, for example, filtration, extraction or distillation. The compounds prepared in this way can be handled in the usual manner.

The process can be carried out in the presence or absence of aprotic solvents. If aprotic solvents are used, solvents or solvent mixtures having a boiling point or boiling range of up to 120° C. at 0.1 MPa are preferred. Examples of such solvents include ethers such as dioxane, tetrahydrofuran, diethyl ether, diisopropyl ether and diethylene glycol dimethyl ether; chlorinated hydrocarbons such as dichloromethane, trichloromethane, tetrachloromethane, 1,2-dichloroethane, and trichloroethylene; hydrocarbons such as pentane, n-hexane, hexane isomer mixtures, heptane, octane, petroleum benzine, petroleum ether, benzene, toluene and xylene; ketones such as acetone, methyl ethyl ketone, diisopropyl ketone and methyl isobutyl ketone (MIBK); esters such as ethyl acetate, butyl acetate, propyl propionate, ethyl butyrate and ethyl isobutyrate; carbon disulfide; and nitrobenzene, or mixtures of these solvents.

All the symbols in the above formulae have their meanings in each case independently of one another.

In the following examples, unless stated otherwise, all amounts and percentages are by weight, all pressures are 0.10 MPa (abs.) and all temperatures are 20° C.

EXAMPLE 1

Amination of 3-chloropropyldimethylchlorosilane 28.2 g (0.165 mol) of 3-chloropropyldimethylchlorosilane were introduced into a 0.3 1 autoclave fitted with thermocouple, stirrer and pressure gauge and the autoclave was sealed. 78 g (4.581 mol) of ammonia (28-fold excess) were injected at 10° C. over the course of 3 minutes, and the mixture was subsequently heated to 106° C. by means of an oil bath over the course of 50 minutes with stirring. A pressure of 65–67 bar became established in the process. After cooling, the excess of ammonia was slowly vented, and after 4 hours the autoclave was opened. The product and ammonium chloride were in the form of a pale yellow suspension, which could be poured out of the autoclave after agitating with pentane (2×70 ml). After filtration and rinsing twice with pentane, the filtrate was evaporated and distilled at 70° C. and 100 mbar.

Yield: 17.85 g of N-((3-aminopropyl)dimethylsilyl)-2,2-dimethyl-1-aza-2-silacyclopentane. - $^1$H-NMR (CDCl$_3$, 25° C.): δ=0.00 (s, 6 H, H$_2$NCH$_2$CH$_2$CH$_2$Si(CH$_3$)$_2$), 0.05 (s, 6 H, NCH$_2$CH$_2$CH$_2$Si(CH$_3$)$_2$), 0.45 (m, 2 H, H$_2$NCH$_2$CH$_2$CH$_2$Si(CH$_3$)$_2$), 0.59 (t, 2 H, NCH$_2$CH$_2$CH$_2$Si(CH$_3$)$_2$), 1.00 (s, 2 H, H$_2$NCH$_2$CH$_2$CH$_2$Si(CH$_3$)$_2$), 1.36 (m, 2 H, H$_2$NCH$_2$CH$_2$CH$_2$Si(CH$_3$)$_2$), 1.65 (q, 2 H, NCH$_2$CH$_2$CH$_2$Si(CH$_3$)$_2$), 2.62 (t, 2 H, H$_2$NCH$_2$CH$_2$CH$_2$Si(CH$_3$)$_2$), 2.88 (t, 2 H, NCH$_2$CH$_2$CH$_2$Si(CH$_3$)$_2$). - $^{29}$Si-{$^1$H}-NMR (CDCl$_3$, 25° C.): δ=3.3 (s, H$_2$NCH$_2$CH$_2$CH$_2$Si(CH$_3$)$_2$), 18.5 (s, NCH$_2$CH$_2$CH$_2$Si(CH$_3$)$_2$).

EXAMPLE 2

Amination of bis (3-chloropropyl)tetramethyldisilazane

As described above, 23.74 g (0.083 mol) of bis(3-chloropropyl)tetramethyldisilazane and 78 g (4.5 mol) of ammonia (54-fold excess) were stirred in an autoclave at 105–107° C. for a reaction duration of 3 hours. The crude product was worked up as in Example 1.

Yield: 17.24 g of N-((3-aminopropyl)dimethylsilyl)-2,2-dimethyl-1-aza-2-silacyclopentane.

EXAMPLE 3

Amination of bis (3-chloropropvyl)tetramethvldisilazane 30 g of an 80% solution of the silazane used in Example 2 in tert-butyl methyl ether were reacted with 78 g of ammonia in an autoclave. The work-up was as in Example 1, giving 16.33 g of N-((3-aminopropyl)dimethylsilyl)-2,2-dimethyl- 1-aza-2-silacyclopentane.

EXAMPLE 4

Hydrolysis of cyclic silazane to give bisaminoalkvl-terminated disiloxane 23 g (100 mmol) of N-((3-aminopropyl)dimethylsilyl)-2,2-dimethyl-1-aza-2-silacyclopentane were dissolved in 50 ml of THF, and 4 ml of water were subsequently added with ice cooling. Distillation gave 23.6 g of bis(3-aminopropyl) tetramethyldisiloxane (95% yield).

EXAMPLE 5

Alcoholysis of cyclic silazane to give aminoalkyl-terminated dimethylmethoxysilane 23 g (100 mmol) of N-((3-aminopropyl)dimethylsilyl)-2,2-dimethyl-1-aza-2-silacyclopentane were dissolved in 50 ml of THF, and 30 ml of methanol were subsequently added with ice cooling. Distillation gave 28 g of aminopropyl-dimethylmethoxysilane (95% yield).

What is claimed is:

1. A cyclic silazane of the general formula II

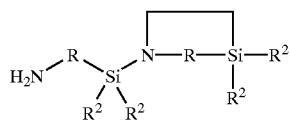

(II)

in which

R is a divalent, Si—C— and C—N-bound, optionally cyano- or halogen-substited C$_3$–C$_{15}$-hydrocarbon radical, in which one or more non-adjacent methylene units are optionally replaced by —O—, —CO—, —COO—, —OCO—, —OCOO—, —S— or —NR$^x$— groups and in which one or more non-adjacent methine units are optionally replaced by —N=, —N=N— or —P= groups, where at least 3 and at most 6 atoms are positioned in the silazane ring between the silicon atom and the nitrogen atom, R$^x$ is hydrogen or an optionally halogen-substituted C$_1$–C$_{10}$–hydrocarbon radical, and R$^2$ is a hydrogen atom or a monovalent, optionally cyano- or halogen-substituted, Si-C- bound C$_1$–C$_{20}$-hydrocarbon radical or C$_1$–C$_{20}$-hydrocarbonoxy radical, in each of which one or more non-adjacent methylene units are optionally replaced by —O—, —CO—, —COO—, —OCO—, —OCOO—, —S— or —NR$^x$— groups and in which one or more non-adjacent methine units are optionally replaced by —N=, —N=N— or —P= groups.

2. The cyclic silazane of claim 1, in which R is an unbranched C$_3$–C$_4$-alkylene radical.

3. The cyclic silazane of claim 1, in which R$^2$ is selected from the radicals methyl, ethyl, phenyl, vinyl and trifluoropropyl.

4. The cyclic silazane of claim 2, in which R$^2$ is selected from the radicals methyl, ethyl, phenyl, vinyl and trifluoropropyl.

5. A process for the preparation of a cyclic silazane of the general formula II as claimed in claim 1, comprising reacting:

(A) a haloalkyldialkylchlorosilane of the general formula IV

(IV)

or a bishaloalkyltetraalkyldisilazane of the general formula V

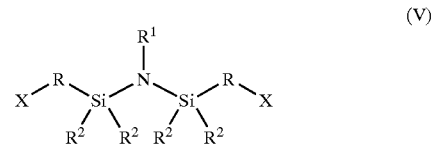

(V)

or a mixture of compounds of the general formulae IV and V, in which

X is F, Cl, Br or I,

R$^1$ is a hydrogen atom or a monovalent, optionally halogen-substituted, Si—C-bound C$_1$–C$_{15}$-hydrocarbon radical in which in each case one or more non-adjacent methylene units are optionally replaced by —O—, —CO—, —COO—, —OCO—, —OCOO— or —S— groups and in which one or more non-adjacent methine units are optionally replaced by —N=, —N=N— or —P= groups, and R$^2$ and R are as defined in claim 1, with (B) ammonia.

6. The process of claim 5, in which ammonia is employed in a 10- to 140-fold molar excess based on the compounds of the general formulae IV and V.

7. A process for the preparation of a bisaminoalkyl-terminated disiloxane of the general formula III

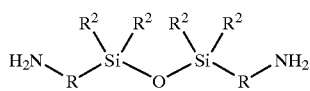

(III)

said process comprising hydrolyzing a compound of the general formula II as claimed in claim 1.

8. A process for the preparation of an aminoalkyl-terminated dialkylalkoxysilane of the general formula VI

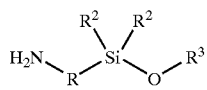

(VI)

in which a compound of the general formula II as claimed in claim 1 is reacted with an alcohol of the general formula $R^3$—OH, where $R^3$ is a monovalent, optionally cyano- or halogen-substituted $C_1$–$C_{20}$-hydrocarbon radical, in which one or more non-adjacent methylene units are optionally replaced by —O—, —CO—, —COO—, —OCO—, —OCOO—, —S— or —$NR^x$-groups and in which one or more non-adjacent methine units are optionally replaced by —N═, —N═N— or —P═ groups and which optionally bears OH groups.

* * * * *

UNITED STATES PATENT AND TRADEMARK OFFICE
CERTIFICATE OF CORRECTION

PATENT NO.     : 6,531,620 B2
DATED          : March 11, 2003
INVENTOR(S)    : Leonhard Brader et al.

It is certified that error appears in the above-identified patent and that said Letters Patent is hereby corrected as shown below:

<u>Column 8,</u>
Line 7, please delete the number "8".

Signed and Sealed this

Fifth Day of August, 2003

JAMES E. ROGAN
*Director of the United States Patent and Trademark Office*